(12) United States Patent
Sun

(10) Patent No.: US 7,491,306 B2
(45) Date of Patent: Feb. 17, 2009

(54) APPARATUS FOR USE IN GEL ELECTROPHORESIS

(76) Inventor: Xiumei Sun, 454 N. 34th St., Seattle, WA (US) 98103

( * ) Notice: Subject to any disclaimer, the term of this patent is extended or adjusted under 35 U.S.C. 154(b) by 103 days.

(21) Appl. No.: 11/184,115

(22) Filed: Jul. 19, 2005

(65) Prior Publication Data

US 2007/0017813 A1 Jan. 25, 2007

(51) Int. Cl.
G01N 27/453 (2006.01)
B65D 85/38 (2006.01)
B65D 1/34 (2006.01)
B65D 6/00 (2006.01)

(52) U.S. Cl. .................. 204/616; 206/305; 206/555; 220/4.09

(58) Field of Classification Search ............. 210/4.09, 210/4.08, 4.28; 206/305, 555, 783, 557; 204/450, 466, 470, 600, 616, 620
See application file for complete search history.

(56) References Cited

U.S. PATENT DOCUMENTS

| | | | |
|---|---|---|---|
| 4,151,065 A * | 4/1979 | Kaplan et al. ............... | 204/620 |
| 4,347,934 A | 9/1982 | Goodman | |
| 4,415,418 A | 11/1983 | Turre et al. | |
| 4,756,809 A | 7/1988 | Love et al. | |
| 4,911,816 A | 3/1990 | Love et al. | |
| 4,933,216 A * | 6/1990 | Filbert et al. ............... | 428/34.1 |
| 5,013,064 A * | 5/1991 | Miller et al. ............. | 280/730.1 |
| 5,443,704 A | 8/1995 | Kirkpatrick et al. | |
| 5,582,702 A | 12/1996 | Cabilly et al. | |
| 5,753,095 A | 5/1998 | Alpenfels et al. | |
| 5,885,431 A | 3/1999 | Renerew et al. | |
| 5,938,906 A | 8/1999 | Moi et al. | |
| 6,036,021 A | 3/2000 | Moi | |
| 6,558,521 B1 | 5/2003 | Riley et al. | |
| 6,576,109 B1 * | 6/2003 | Hsu ........................... | 204/616 |
| 6,682,641 B1 | 1/2004 | Finney et al. | |
| 6,863,175 B2 | 3/2005 | Gelardi | |
| 6,913,462 B2 | 7/2005 | Honstein et al. | |

FOREIGN PATENT DOCUMENTS

GB 1563391 * 3/1980
GB 2269808 A * 2/1994

* cited by examiner

Primary Examiner—Alex Noguerola
(74) Attorney, Agent, or Firm—Jensen & Puntigam, P.S.

(57) ABSTRACT

An apparatus for use in conducting gel electrophoresis. The apparatus includes a gel matrix and a tray for containing the gel. The tray consists of a bottom surface, opposed side walls and opposed end walls. The side walls are connected to the bottom surface and the end walls by frangible joints such that the side walls may be completely detached from the tray for ease of use.

11 Claims, 4 Drawing Sheets

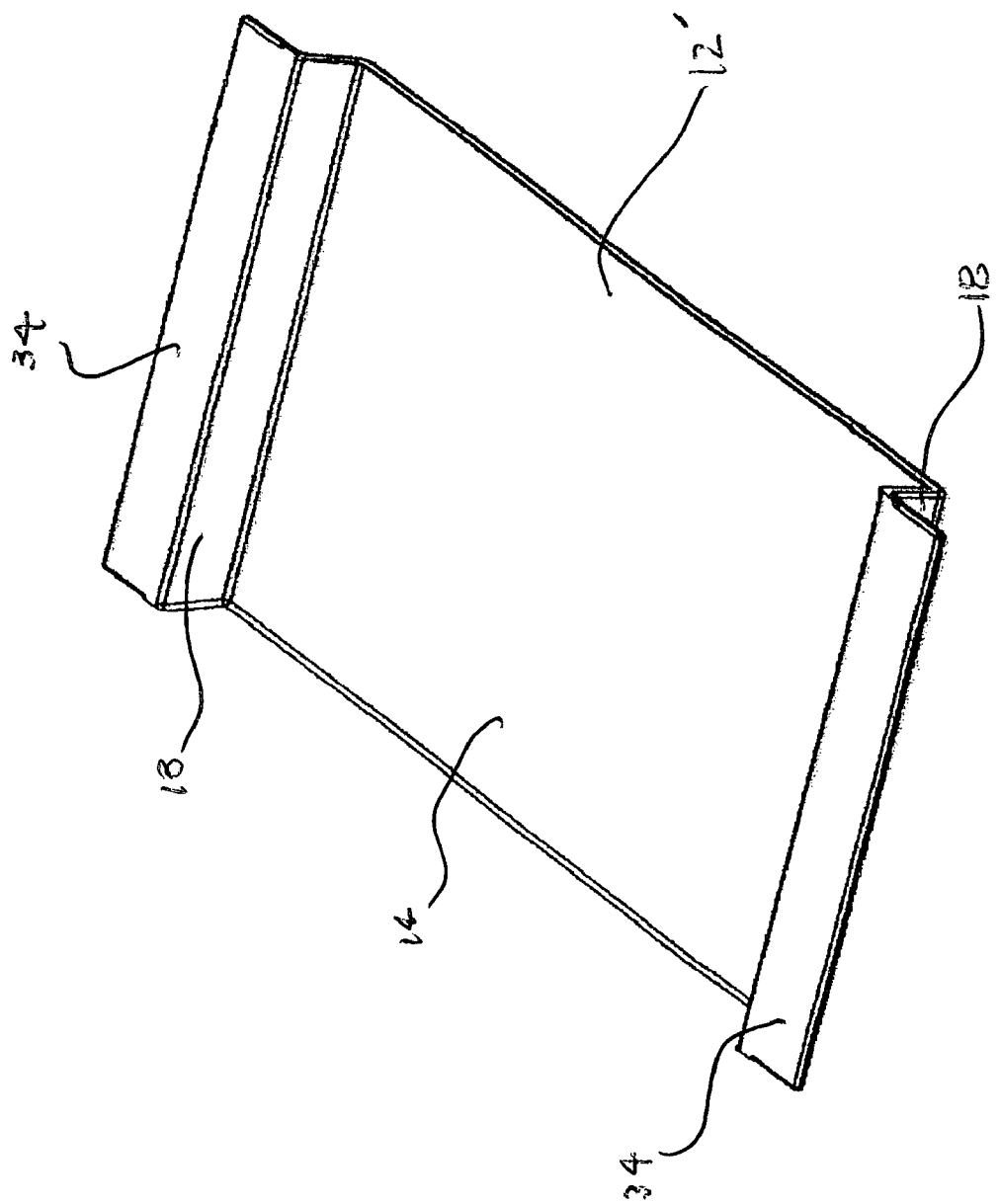

APPARATUS FOR USE IN GEL ELECTROPHORESIS

BACKGROUND OF THE INVENTION

1. Field of the Invention

This invention relates generally to electrophoresis gel trays, and, in particular, to an improved gel tray having frangible sections which improve handling and use of electrophoresis gels.

2. Description of the Related Art

The separation of micromolecules in an electric field is known as electrophoresis. Gel electrophoresis is a common procedure for the separation of biological materials, such as DNA, RNA, polypeptides and proteins. In gel electrophoresis, the molecules are separated into bands according to the rate at which the electric field causes them to migrate through the gel.

In the past, it was common for laboratories to prepare gels for use; however, prefabricated gels for use in research laboratories are currently very popular. A prepackaged gel provides a faster, more uniform and efficient method for performing gel electrophoresis.

One problem with prefabricated gels is that they are very fragile. These gels must be handled delicately, and are subject to cracking or breaking if not handled with utmost care. In addition, prefabricated gels must be adequately packed for shipment to prevent damage in transit.

U.S. Pat. No. 6,558,521 addresses the problem of containing and protecting electrophoresis gels during handling, storage, and shipment. The packaging arrangement includes first and second sheets that are sealed along their respective edges to form an enclosed cavity. The cavity may be at least partially evacuated of air prior to sealing, causing the top and bottom sheets to conform to the gel, restraining it from movement within the package. In another embodiment, the gel is located within a tray which is located between the top and bottom sheets. A combination of the low pressure environment in the package and the tray produces a rigid packaging configuration that minimizes motion of the electrophoresis gel contained therein.

A drawback to the use of a prepackaged electrophoresis gel tray is the fact that often it is necessary to remove the gel in order to provide an electric field to perform electrophoresis, as the tray may not allow current to pass. Often, it is necessary to use a scissors to cut away part of the tray to run the electrophoresis. In this case, the gel must be removed to cut the tray, and then replaced within the tray, increasing the possibility of damage to the gel. If this is not done, then it takes much longer to run the electrophoresis, which could affect the background of the DNA.

OBJECT OF THE INVENTION

It is therefore an object of the present invention to provide an electrophoresis gel tray which can be completed to an electric field without removing the gel from the tray.

It is also an object of the present invention to provide an electrophoresis gel tray which allows handling of the gel without damaging the gel while maintaining the moisture status of the gel.

It is a still further object of the present invention to provide an electrophoresis gel tray which can be used directly without modification by tools.

It is a still further object of the present invention to provide an electrophoresis gel tray which is inexpensive and requires minimal handling.

These and other objects of the present invention will be more readily apparent from the enclosed description and drawings.

BRIEF DESCRIPTION OF THE DRAWINGS

FIG. 5 is a perspective view of the tray of FIG. 3 with the sides removed.

DETAILED DESCRIPTION OF THE INVENTION

Figure 1:
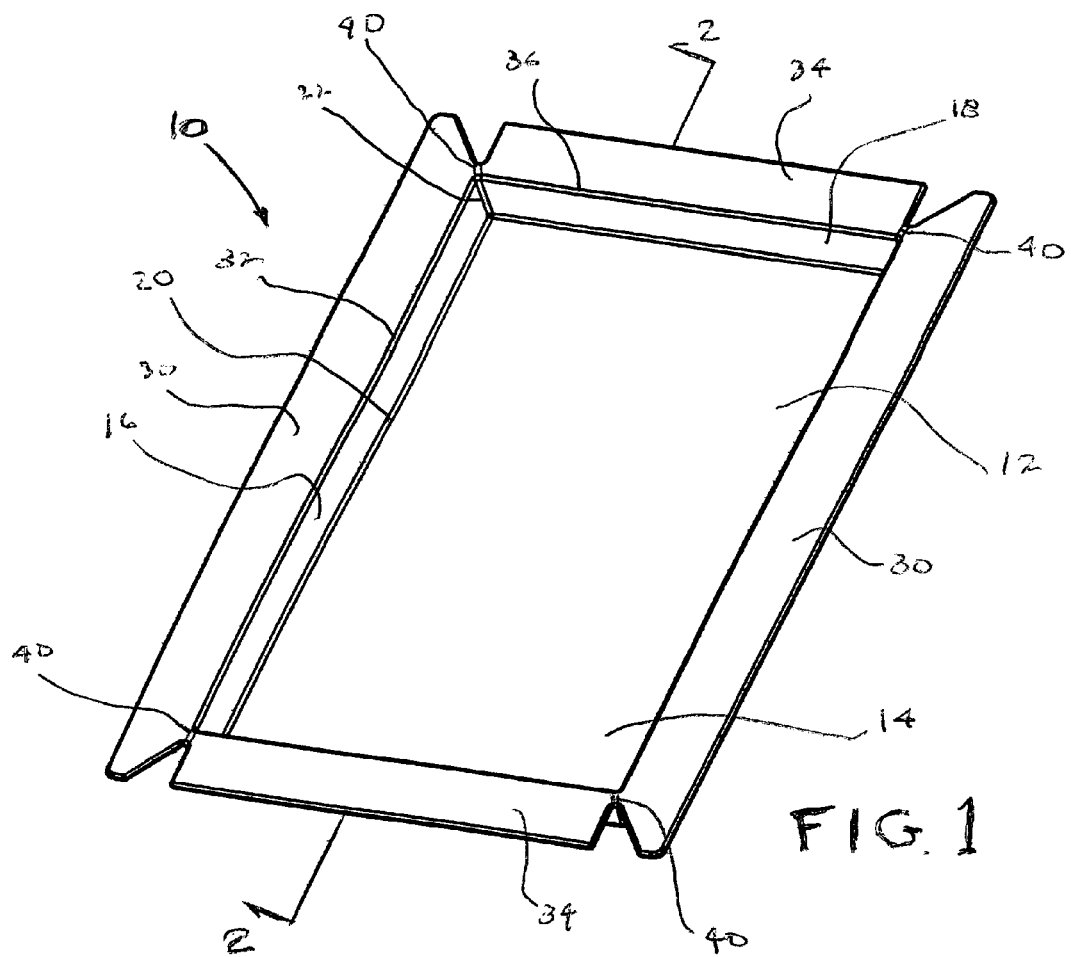
FIG. 1 is a perspective view of a tray according to the present invention.

Referring now to FIG. 1, there is shown a gel electrophoresis apparatus, generally designated at 10, which is constructed according to the present invention. Apparatus 10 includes a tray 12 having a bottom surface 14, a pair of opposed upstanding side walls 16, and a pair of opposed upstanding end walls 18. A pair of frangible joints 20 attach side walls 16 to bottom surface 14. Joints 20 have a thickness which is less than the thickness of bottom surface 14 or side walls 16, which allows joints 20 to possess rigidity while allowing side walls 16 to be easily detached from bottom surface 14. In the present embodiment, bottom surface 14 and side walls 16 possess a thickness of approximately 1 millimeter, while the thickness of joint 20 ranges from approximately 0.3 to 0.5 millimeters.

Frangible joints 22 connect side walls 16 to end walls 18 in each of the corners of apparatus 10. Joints 22 also have a thickness of from approximately 0.3 to 0.5 millimeters, allowing side walls 16 to be detached from end walls 18 neatly and easily.

Joints 24 connect end walls 18 to bottom surface 14 at each end of apparatus 10. These joints have the same thickness as bottom surface 14 and end walls 18, holding these surfaces together.

Apparatus 10 also contains a pair of outwardly extending side ledges 20 which are each connected to the upper edge of a side wall 16 along a joint 32. Ledges 30 may be used in handling apparatus 10 without a risk of contaminating the gel contained within apparatus 10.

Apparatus 10 also contains a pair of outwardly extending end ledges 34 which are each connected to the upper edge of an end wall 18 along a joint 36. Joints 36 may also have a reduced thickness which will allow ledges 34 to be easily detached from end walls 18. Ledges 30 and 34 may be used in sealing apparatus 10 for shipment without a risk of contaminating the gel, which keeps the gel moist. Ledges 34 may also be used to hold tray 12 on the electrophoresis device.

The intersection of ledges 30 and 34 each contain a joint 40 located at each corner of apparatus 10. Each joint 40, which contain a lesser material thickness than that of bottom surface 14, aid in separating side walls 16 from bottom surface 12.

Figure 2:
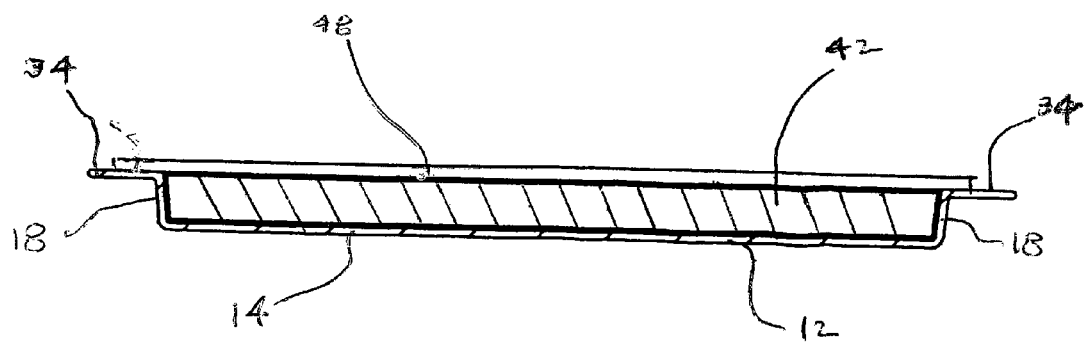
FIG. 2 is a cross-sectional view taken along lines of FIG. 1 which includes an electrophoresis gel.

FIG. 2 represents apparatus 10 after tray 12 has been filled with a gel for performing electrophoresis. In the present embodiment, a gel 42 has been cast within tray 12 such that it fills tray 12 to a level which approximates a plane through ledges 30 and 34. Gel 42 is preferably an agarose gel which is available in a range of concentrations. Gel 42 may alternatively consist of acrylamide, or any other gel suitable for use in gel electrophoresis. A thin sheet 48 may be used to seal gel 42 within tray 12 by attaching sheet 48 over gel 42 in tray 12 to ledges 30, 34. Sheet 48, which may be made from a polyester or polypropylene material, acts to protect gel 42 from environmental factors, thus maintaining the proper moisture content.

Figure 3:
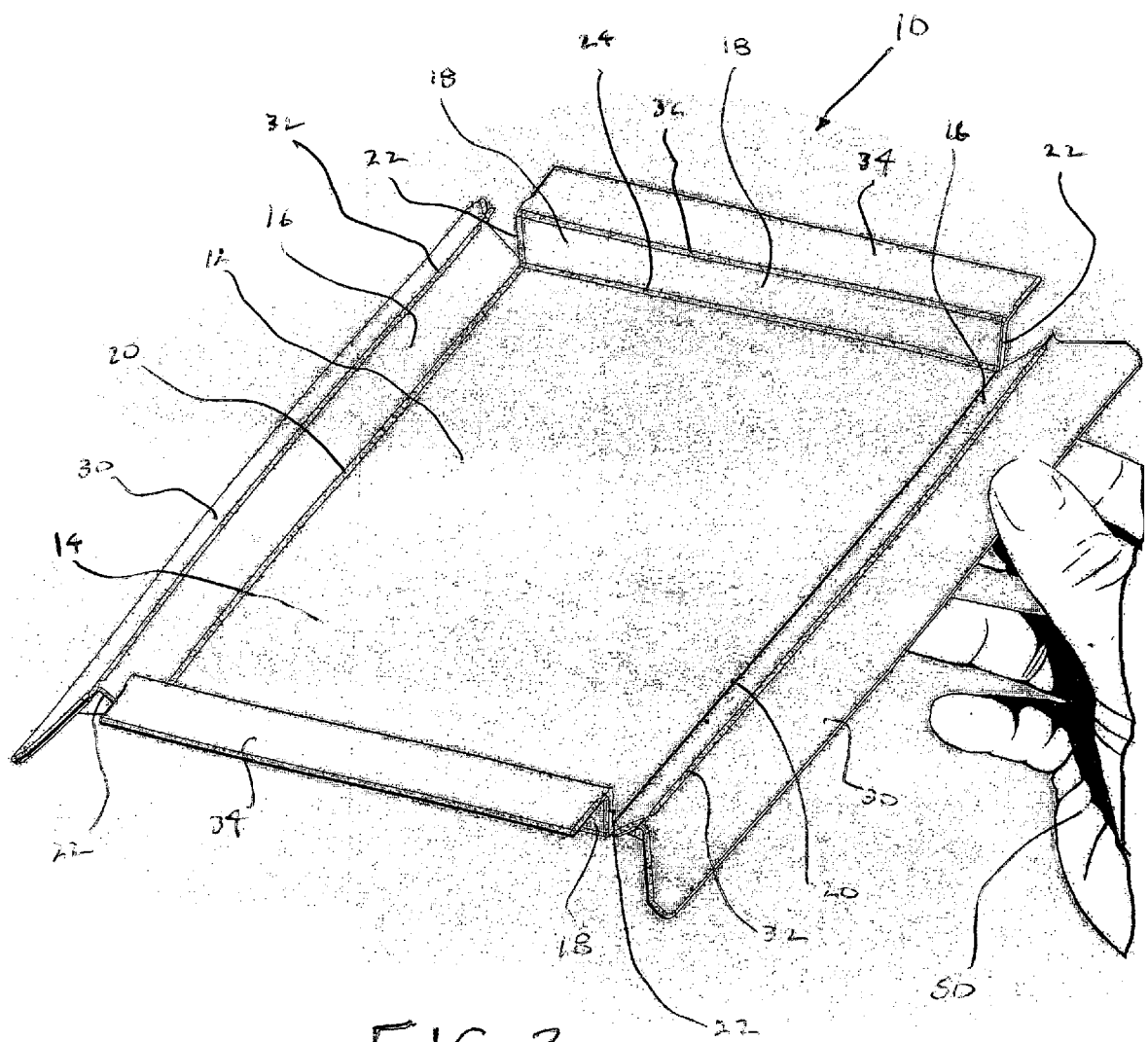
FIG. 3 is a perspective view of a tray according to the present invention showing the frangible sides.

FIG. 3 shows the apparatus of the present invention in preparation for use in gel electrophoresis. Although gel 42 is not shown within tray 12 in FIG. 3, it will be understood that gel 42 is present within tray 12 during the procedure to be described. Referring now to FIG. 3, the hand 50 of a user grips ledge 30 of tray 12, and applies sufficient downward pressure to detach side wall 16 at joints 40 and 22 to separate side wall 16 from end walls 18. Continued downward pressure by hand 50 will cause side wall 18, connected to ledge 30, to completely separate from bottom surface 14. The user then repeats this procedure on the opposite side wall 16, such that both side walls 16 have been removed, and apparatus 10 is ready for the electrophoresis separation procedure.

Figure 4:
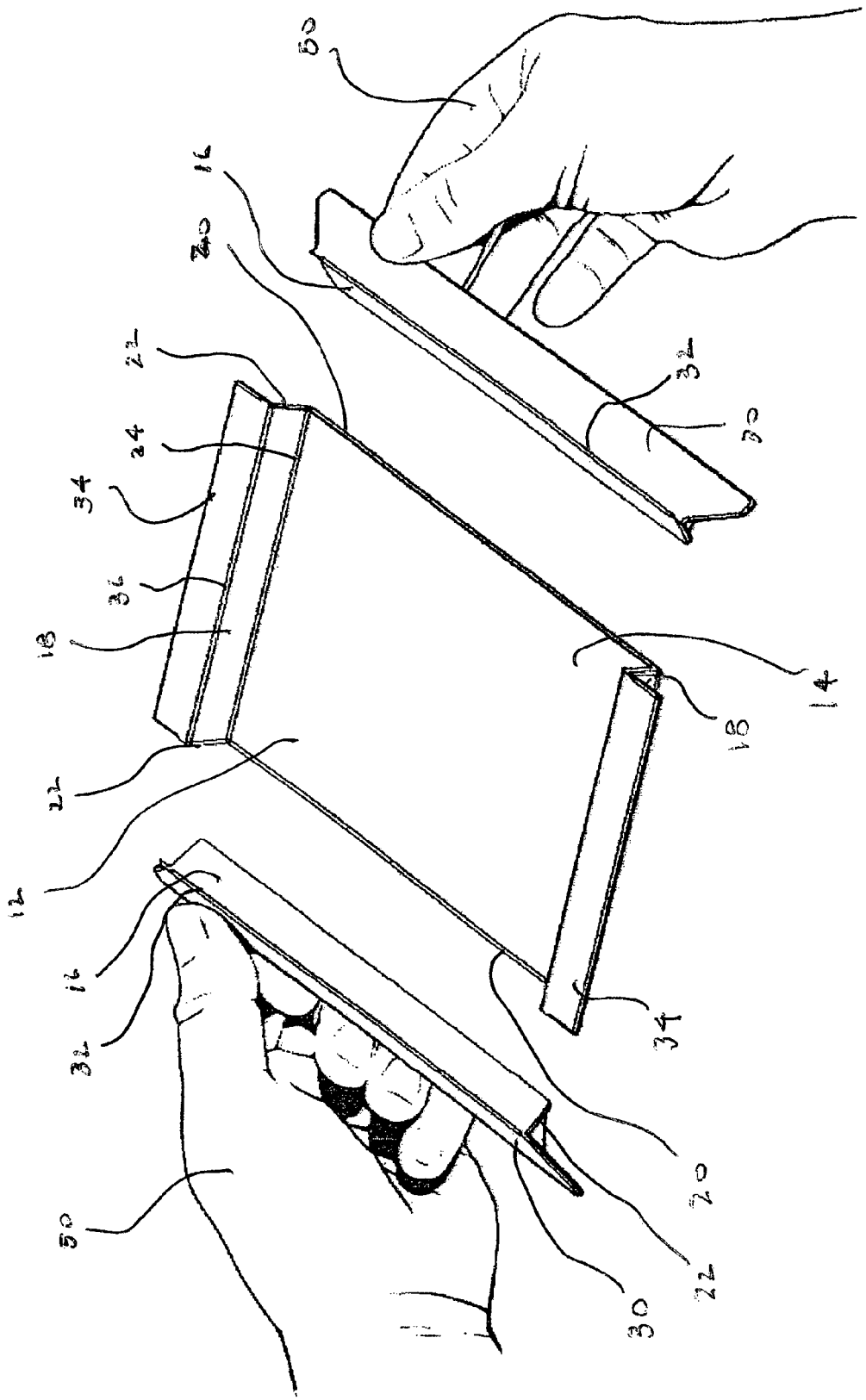
FIG. 4 is a perspective view of the tray of FIG. 3 showing removal of the sides.

FIG. 4 shows the apparatus of the present invention having its sides removed. Each side wall 16 with its corresponding ledge 30 has been detached from bottom surface 14 of tray 12 along joint 20, and is held in a hand 50. The resultant tray 12' is shown in FIG. 5. Tray 12' comprises bottom surface 14, end walls 18, and ledge 34. Gel 42, which remained within tray 12' while side walls 16 were removed, is now ready for performing gel electrophoresis.

In the above description, and in the claims which follow, the use of such words as "upper", "lower", "clockwise", "counterclockwise", "distal", "proximal", "forward", "outward", "rearward", "vertical", "horizontal", and the like is in conjunction with the drawings for purposes of clarity.

The foregoing description of the preferred embodiments of the invention has been presented for purposes of illustration and description. It is not intended to be exhaustive or limit the invention to the precise form disclosed, and many modifications and variations for the device are possible in light of the above teaching. The embodiment was chosen and described in order to best explain the principles of the invention and its practical application to thereby enable others skilled in the art to best utilize the invention and various embodiments and with various modifications as are suited to the particular use contemplated. It is intended that the scope of the invention be defined by the claims appended hereto.

What is claimed is:

1. An apparatus for use in performing gel electrophoresis, comprising:
    a gel tray, comprising:
      a bottom surface;
      a pair of upstanding opposed side walls attached to said bottom surface; and
      a pair of upstanding opposed end walls attached to said bottom surface and said side walls;
    and an electrophoresis gel matrix, contained within said tray, having an upper surface, a lower surface, a pair of opposing side walls and a pair of opposing end walls;
    wherein said side walls of said tray are attached to said bottom surface and said end walls by frangible joints along which each side wall may be detached to allow access to said electrophoresis gel.

2. The apparatus of claim 1, wherein said electrophoresis gel comprises an agarose gel.

3. The apparatus of claim 1, wherein said electrophoresis gel comprises a polyacrylamide gel.

4. The apparatus of claim 1, wherein said opposed side walls each contain an outwardly extending side ledge located along the upper edge of said side wall.

5. The apparatus of claim 1, wherein said opposed end walls each contain an outwardly extending end ledge located along the upper edge of said end wall.

6. The apparatus of claim 5, wherein said ledges and said end ledges are attached by a plurality of second frangible joints.

7. The apparatus of claim 1, wherein the thickness of said bottom surface, side walls, and end walls is approximately 1 millimeter.

8. The apparatus of claim 7, wherein the thickness of said frangible joints is between approximately 0.3 to 0.5 millimeters.

9. The apparatus of claim 7, further comprising a thin sheet attached to said side ledges and said end ledges to seal said gel matrix from environmental factors.

10. The apparatus of claim 9, wherein said thin sheet comprises a polypropylene material.

11. The apparatus of claim 1, wherein said tray is constructed from an acrylic plastic.

* * * * *